United States Patent
Berthelette et al.

(10) Patent No.: US 7,317,036 B2
(45) Date of Patent: Jan. 8, 2008

(54) FLUORO SUBSTITUTED CYCLOALKANOINDOLES, COMPOSITIONS CONTAINING SUCH COMPOUNDS AND METHODS OF TREATMENT

(75) Inventors: Carl Berthelette, Ste-Dorothee Laval (CA); Nicolas Lachance, Pierrefonds (CA); Lianhai Li, Pierrefonds (CA); Claudio Sturino, L'ile-Bizard (CA); Zhaoyin Wang, Kirkland (CA)

(73) Assignee: Merck Frosst Canada & Co., Kirkland, Quebec (CA)

( * ) Notice: Subject to any disclaimer, the term of this patent is extended or adjusted under 35 U.S.C. 154(b) by 151 days.

(21) Appl. No.: 10/502,380

(22) PCT Filed: Jan. 22, 2003

(86) PCT No.: PCT/CA03/00084

§ 371 (c)(1),
(2), (4) Date: Jan. 28, 2005

(87) PCT Pub. No.: WO03/062200

PCT Pub. Date: Jul. 31, 2003

(65) Prior Publication Data

US 2005/0124680 A1 Jun. 9, 2005

Related U.S. Application Data

(60) Provisional application No. 60/351,384, filed on Jan. 24, 2002.

(51) Int. Cl.
*A61K 31/403* (2006.01)
*C07D 209/88* (2006.01)
(52) U.S. Cl. ..................... 514/411; 548/443
(58) Field of Classification Search ............... 548/427, 548/439; 514/411
See application file for complete search history.

(56) References Cited

U.S. PATENT DOCUMENTS

| | | |
|---|---|---|
| 3,535,326 A | 10/1970 | Yamamoto et al. |
| 3,862,953 A | 1/1975 | Berger et al. |
| 4,009,181 A | 2/1977 | Berger et al. |
| 4,057,559 A | 11/1977 | Asselin et al. |
| 4,775,680 A | 10/1988 | Gillard et al. |
| 4,808,608 A | 2/1989 | Guindon et al. |
| 4,940,719 A | 7/1990 | Gillard et al. |
| 5,021,447 A | 6/1991 | Guindon et al. |
| 6,410,583 B1 | 6/2002 | Labelle et al. |
| 7,019,022 B2 * | 3/2006 | Beaulieu et al. ............ 514/411 |
| 2003/0158246 A1 | 8/2003 | Berthelette et al. |

* cited by examiner

*Primary Examiner*—Kamal A. Saeed
(74) *Attorney, Agent, or Firm*—Richard C. Billups; Mollie M. Yang; Catherine D. Fitch

(57) ABSTRACT

Fluoro substituted cycloalkanoindole derivatives are antagonists of prostaglandins, and as such are useful for the treatment of prostaglandin mediated diseases.

6 Claims, No Drawings

FLUORO SUBSTITUTED CYCLOALKANOINDOLES, COMPOSITIONS CONTAINING SUCH COMPOUNDS AND METHODS OF TREATMENT

CROSS REFERENCE TO RELATED APPLICATIONS

This application is the National Stage of International Application No. PCT/CA03/00084, filed 22 Jan. 2003 which claims the benefit under 35 U.S.C. 119(e) of U.S. Provisional Application No. 60/351384, filed 24 Jan. 2002.

BACKGROUND OF THE INVENTION

The present invention relates to compounds and methods for treating prostaglandin mediated diseases, and certain pharmaceutical compositions thereof. More particularly, the compounds of the invention are structurally different from steroids, antihistamines or adrenergic agonists, and are antagonists of the nasal and pulmonary congestion effects of D-type prostaglandins.

Two review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137-154 and Journal of Lipid Mediators and Cell Signalling, 1996, 14, 83-87. An article from T. Tsuri et al. published in 1997 in Journal of Medicinal Chemistry, vol 40, pp.3504-3507 states that "PGD2 is considered to be an important mediator in various allergic diseases such allergic rhinitis, atopic asthma, allergic conjunctivitis and atopic dermatitis." More recently, an article by Matsuoka et al. in *Science* (2000), 287:2013-7, describes PGD2 as being a key mediator in allergic asthma. In addition, patents such as U.S. Pat. No. 4,808,608 refer to prostaglandin antagonists as useful in the treatment of allergic diseases, and explicitly allergic asthma. PGD2 antagonists are described in, for example, European Patent Application 837,052 and PCT Application WO98/25919, as well as WO99/62555.

U.S. Pat. No. 4,808,608 discloses tetrahydrocarbazole-1-alkanoic acid derivatives as prostaglandin antagonists.

PCT Application WO0179169 discloses PGD2 antagonists having the formula:

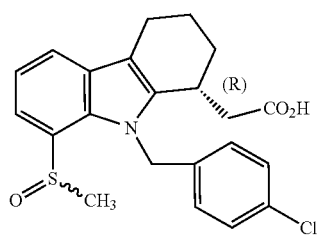

European Patent Application 468,785 discloses the compound 4-[(4-chlorophenyl(methyl]-1, 2,3,4-tetrahydro-7-(2-quinolinylmethoxy)-cyclopent[b]indole-3-acetic acid, which is a species of a genus said to be leukotriene biosynthesis inhibitors.

U.S. Pat. No. 3,535,326 discloses antiphlogistic compounds of the formula:

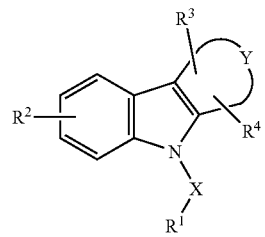

SUMMARY OF THE INVENTION

The present invention provides novel compounds which are prostaglandin receptor antagonists; more particularly, they are prostaglandin D2 receptor (DP receptor) antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

DETAILED DESCRIPTION OF THE INVENTION

The present invention relates to compounds of formula I:

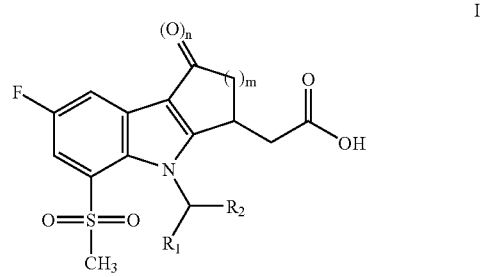

and pharmaceutically acceptable salts thereof, wherein n is 0 or 1; m is 1, 2 or 3; $R_1$ is H, $C_1$-$C_3$ alkyl, halogenated $C_1$-$C_3$ alkyl or cyclopropyl; $R_2$ is 4-chlorophenyl or 2,4,6-trichlorophenyl.

In one embodiment of formula I are compounds wherein n is 0.

In another embodiment of formula I are compounds wherein n is 1.

In another embodiment of formula I are compounds wherein m is 1.

In another embodiment of formula I are compounds wherein m is 2.

In another embodiment of formula I are compounds wherein $R_1$ is H.

In another embodiment of formula I are compounds wherein $R_1$ is $CH_3$.

In another embodiment of formula I are compounds wherein $R_2$ is 4-chlorophenyl.

In another embodiment of formula I are compounds wherein $R_2$ is 2,4,6-trichlorophenyl.

In another embodiment of formula I are compounds having the stereoconfiguration shown below (i.e. the chiral center has the R configuration):

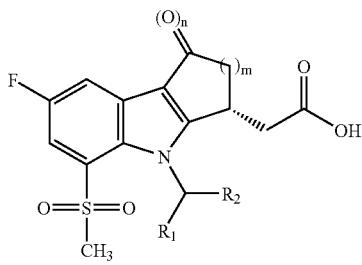

In another aspect of the present invention there is provided pharmaceutical compositions comprising a compound of formula I, and a pharmaceutically acceptable carrier.

In one embodiment, the pharmaceutical compositions further comprises a second active ingredient selected from an antihistamine, a leukotriene antagonist, leukotriene biosynthesis inhibitor, prostaglandin receptor antagonists or biosynthesis inhibitors, corticosteroids, cytokine modulators, anti-IgE, anti-cholinergics or NSAIDS.

In another aspect of the present invention there is provided a method for the treatment or prevention of prostaglandin D2 mediated diseases which comprises administering to a patient in need of treatment a therapeutically effective amount of a compound of formula I.

In one embodiment of the invention is a method of treating or preventing a prostaglandin D2 mediated disease comprising administering to a mammalian patient in need of such treatment a compound of formula I in an amount which is effective for treating or preventing a prostaglandin D2 mediated disease, wherein the prostaglandin mediated disease is nasal congestion, rhinitis including seasonal allergic rhinitis and perennial allergic rhinitis, and asthma including allergic asthma.

In another embodiment of the present invention is a method for the treatment of nasal congestion in a patient in need of such treatment which comprises administering to said patient a therapeutically effective amount of a compound of formula I.

In yet another embodiment of the present invention is a method for the treatment of asthma, including allergic asthma, in a patient in need of such treatment which comprises administering to said patient a therapeutically effective amount of a compound of formula I.

In yet another embodiment of the present invention is a method for the treatment of allergic rhinitis (seasonal and perennial) in a patient in need of such treatment which comprises administering to said patient a therapeutically effective amount of a compound of formula I.

The numbering of the core tricyclic ring system when m is 1 is as shown below:

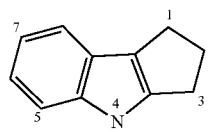

The numbering of the core tricyclic ring system when m is 2 is as shown below:

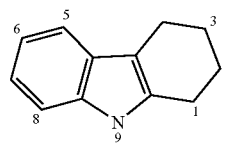

Optical Isomers—Diastereomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid or base as a resolving agent, or by chiral separation techniques such as separation by HPLC using a chiral column.

Alternatively, any enantiomer of a compound of the general formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I are meant to also include the pharmaceutically acceptable salts.

Utilities

Compounds of formula I are antagonists of prostaglandin D2. The ability of compounds of formula I to interact with prostaglandin D2 receptor makes them useful for preventing or reversing undesirable symptoms caused by prostaglandins in a mammalian, especially human subject. The antagonism of the actions of prostaglandin D2 indicates that the compounds and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer. Compounds of formula I may also be of use in the treatment and/or prevention prostaglandin D2 mediated proliferation disorders such as may occur in diabetic retinopathy and tumor angiogenesis. Compounds of formula I may also inhibit prostanoid-induced smooth muscle contraction by antagonizing contractile prostanoids or mimicking relaxing prostanoids and hence may be use in the treatment of dysmenorrhea, premature labor and eosinophil related disorders.

Accordingly, another aspect of the invention provides a method of treating or preventing a prostaglandin D2 mediated disease comprising administering to a mammalian patient in need of such treatment a compound of formula I in an amount which is effective for treating or preventing said prostaglandin D2 mediated disease. Prostaglandin D2 mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; pulmonary hypotension; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases, such as for example atherosclerosis; congestive heart failure; diseases or conditions requiring a treatment of anti-coagulation such as post-injury or post surgery treatment; rheumatoid arthritis and other inflammatory diseases; gangrene; Raynaud's disease; mucus secretion disorders including cytoprotection; pain and migraine; diseases requiring control of bone formation and resorption such as for example osteoporosis; shock; thermal regulation including fever; rejection in organ transplant and by-pass surgery, and immune disorders or conditions in which immunoregulation is desirable. More particularly the disease to be treated is one mediated by prostaglandin D2 such as nasal congestion, allergic rhinitis, pulmonary congestion, and asthma including allergic asthma.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin D2 mediated diseases comprising a therapeutically effective amount of a compound of formula I and one or more other therapeutic agents. Suitable therapeutic agents for combination therapy with a compound of formula I include: (1) a prostaglandin receptor antagonist; (2) a corticosteroid such as triamcinolone acetonide; (3) a β-agonist such as salmeterol, formoterol, terbutaline, metaproterenol, albuterol and the like; (4) a leukotriene modifier, such as a leukotriene antagonist or a lipooxygenase inhibitor such as montelukast, zafirlukast, pranlukast, or zileuton; (5) an antihistamine (histamine H1 antagonist) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, norastemizole, terfenadine, loratadine, cetirizine, levocetirizine, fexofenadine, desloratadine, and the like; (6) a decongestant including phenylephrine, phenylpropanolamine, pseudophedrine, oxymetazoline, ephinephrine, naphazoline, xylometazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, ornoprostol or rosaprostol; (9) a diuretic; (10) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors such as celecoxib and rofecoxib, etoricoxib and valdecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2 or BK1) antagonists, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206.

In addition, the invention encompasses a method of treating prostaglandin D2 mediated diseases comprising: administering to a patient in need of such treatment a therapeutically effective amount of the compound of formula I, co-administered with one or more of such ingredients as listed immediately above. The amounts of active ingredients may be those commonly used for each active ingredient when it is administered alone, or in some instances the combination of active ingredients may result in lower dosage for one or more of the active ingredients.

| Abbreviations Used | |
|---|---|
| Ac | acetyl |
| AcOH | acetic acid |
| DDQ | 2,3-dichloro-5,6-dicyano-1,4-benzoquinone |
| DMF | dimethylformamide |
| eq. | equivalent(s) |
| Et | ethyl |
| EtOAc | ethyl acetate |
| EtOH | ethanol |
| HPLC | high pressure liquid chromatography |
| IPA | isopropyl alcohol |
| IPAc | isopropyl acetate |
| Me | methyl |
| MeOH | methanol |
| MHz | megahertz |

| Abbreviations Used | |
|---|---|
| MTBE | methyl t-butyl ether |
| NMP | N-methyl-2-pyrrolidinone |
| NMR | nuclear magnetic resonance |
| THF | tetrahydrofuran |
| TLC | thin-layer chromatography |

METHODS OF SYNTHESIS

Compounds of Formula I of the present invention can be prepared according to the synthetic routes outlined in Schemes 1 to 5 and by following the methods described herein.

Intermediate compounds of Formula IV may be prepared by the method presented in Scheme 1 from an appropriately substituted phenyl hydrazine II. Reaction of II with an appropriate cycloalkanone III (where R is ester group such as an alkyl group) under Fisher Indole or similar conditions gives IV

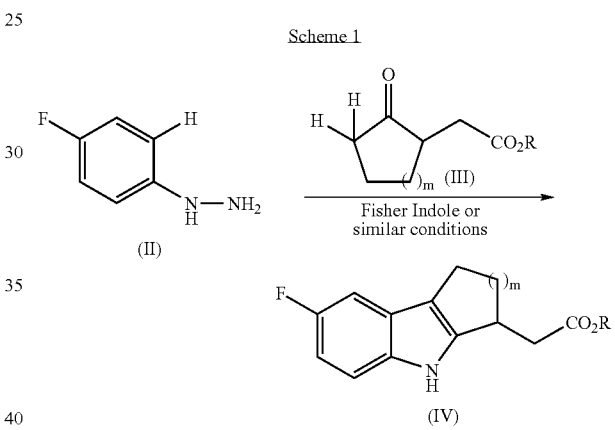

Compounds of Formula IV may alternatively be prepared by the method presented in Scheme 2 from an appropriately substituted aniline V. Condensation of V with an appropriate cycloalkanone III followed by the cyclization under Heck or similar metal catalysis conditions leads to indole IV

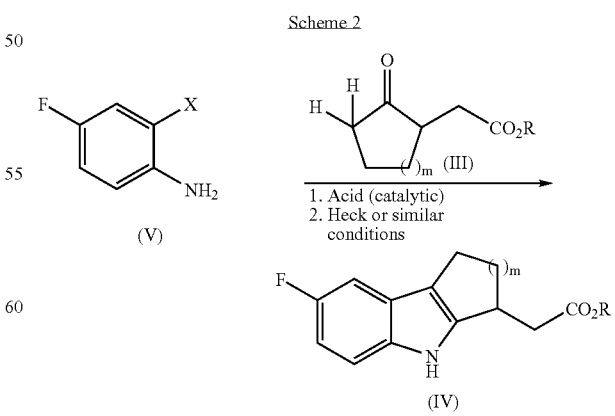

Compounds of Formula III may be prepared by the method presented in Scheme 3 from an appropriately substituted silyl enol ether VI or an appropriately substituted enamine VII. Addition of an appropriate electrophile such as Y—CH$_2$CO$_2$R (wherein Y represents a halogen or a leaving group) in the presence of a base such as an alkyl lithium or a Lewis acid such as silver trifluoroacetate with the silyl enol ether VI gives the cycloalkanone III. The compound of formula III may alternatively be prepared from the addition of Y—CH$_2$CO$_2$R on an appropriately substituted enamine VII under Stork Enamine or similar conditions

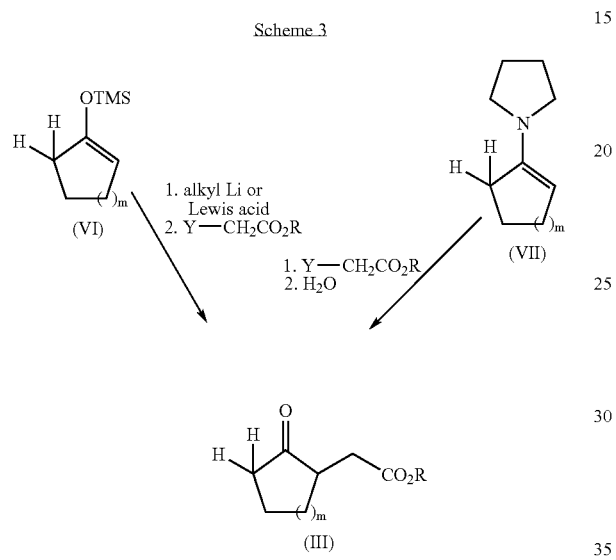

Intermediate compounds of Formula VIII may be prepared by the method presented in Scheme 4 from an appropriately substituted indole IV. Bromination of IV may be accomplished with bromine or a brominating agent such as pyridium tribromide, under basic condition in a polar solvent, for example, by carrying out the reaction in pyridine or in a solvent such as dichloromethane in the presence of pyridine followed by the mono reduction of a dibromo intermediate under acid and reducing metal conditions to generate the bromoindole VIII

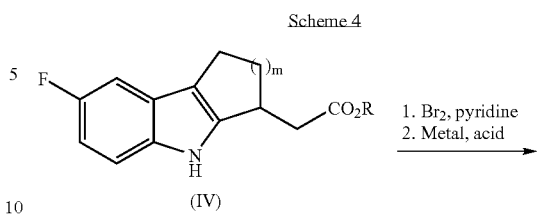

Compounds of Formula I may be prepared by the method presented in Scheme 5 from an appropriately substituted bromoindole VIII. Alkylation of VIII with the appropriate electrophile such as (R$_1$)(R$_2$)CH—Y in the presence of a base and in a suitable solvent such as DMF gives N-alkylated indole IX. Coupling of IX with a methanesulfinate such as sodium methanesulfinate in the presence of Cu(I) salts leads to compounds of formula I, following ester hydrolysis. The bromoindole acid (IX, R═H) may alternatively first react with a suitable metallation agent, such as n-BuLi, followed by trapping with an electrophile such as methyl disulfide to give the corresponding methyl sulfide, which upon oxidation with for example hydrogen peroxide/sodium tungstate provides compound IA. The steps of alkylation of the bromoindole VIII followed by sulfonylation may also be reversed; thus sulfonylation of the bromoindole VIII provides the compound X, which is alkylated using similar conditions as described before or by using Mitsunobu reaction conditions to provide compound of formula IA following ester hydrolysis.

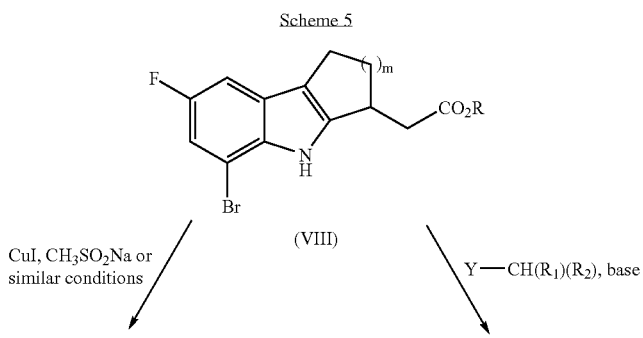

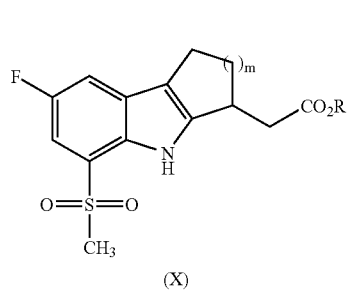 (X)

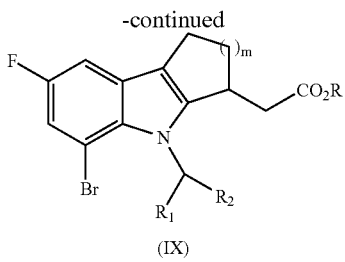 (IX)

Y—CH(R₁)(R₂), base; hydrolysis
or
Mitsunobu conditions with R1R2CHOH

CuI, CH₃SO₂Na or similar conditions; hydrolysis
or
with R = H, BuLi; MeSSMe; H₂O₂/Na₂WO₄

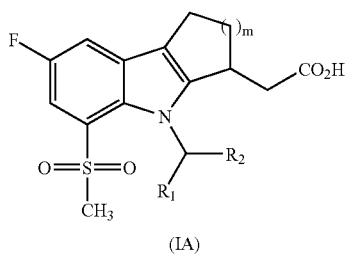 (IA)

Compound IB may be prepared from protected IA, for example an ester of IA, by oxidation using a suitable oxidant followed by hydrolysis, as illustrated in Scheme 6.

Scheme 6

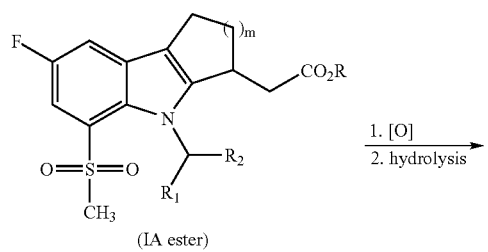

(IA ester)

1. [O]
2. hydrolysis

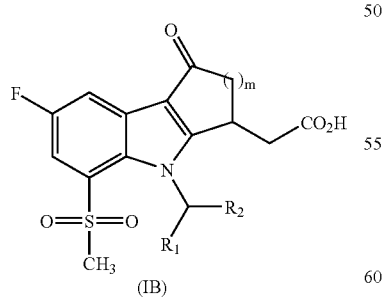 (IB)

Alternatively, IB can be prepared, as illustrated in Scheme 7, by oxidizing IX with a suitable oxidizing agent, such as DDQ, followed by methylsulfonylation as described in Scheme 5 follwed by hydrolysis.

Scheme 7

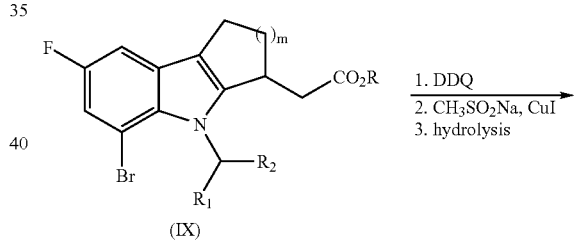 (IX)

1. DDQ
2. CH₃SO₂Na, CuI
3. hydrolysis

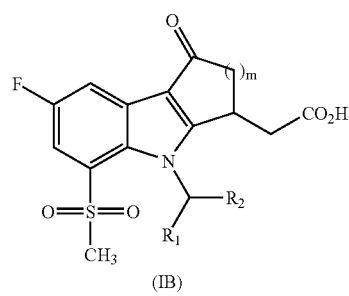 (IB)

Assays for Determining Biological Activity

Compounds of formula I can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences are subcloned into the appropriate sites of mammalian expression vectors and transfected into HEK 293(ebna) cells. HEK 293(ebna) cells expressing the individual cDNAs are grown under selection and individual colonies are isolated after 2-3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 μM of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 μM RO-20174 (phosphodiesterase type IV inhibitor, available from Biomol) and, in the case of the $EP_3$ inhibition assay only, 15 μM forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both $K_B$ and slope values are calculated.

Prevention of PGD2 or Allergen Induced Nasal Congestion in Allergic Sheep

Animal preparation: Healthy adult sheeps (18-50 kg) are used. These animals are selected on the basis of a natural positive skin reaction to an intradermal injection of *Ascaris suum* extract.

Measurements of nasal congestion: The experiment is performed on conscious animals. They are restained in a cart in a prone position with their heads immobilized. Nasal airway resistance (NAR) is measured using a modified mask rhinometry technique. A topical anaesthesia (2% lidocaine) is applied to the nasal passage for the insertion of a nasotracheal tube. The maximal end of the tube is connected to a pneumotachograph and a flow and pressure signal is recorded on an oscilloscope linked to a computer for on-line calculation of NAR. Nasal provocation is performed by the administration of an aerosolized solution (10 puffs/nostril). Changes in the NAR congestion are recorded prior to and for 60-120 minutes post-challenge.

Prevention of PGD2 and Allergen Induced Nasal Obstruction in Cynomolgus Monkey

Animal preparation: Healthy adult male cynomologus monkeys (4-10 kg) are used. These animals are selected on the basis of a natural positive skin reaction to an intradermal injection of *Ascaris suum* extract. Before each experiment, the monkey selected for a study is fasted overnight with water provided at libitum. The next morning, the animal is sedated with ketamine (10-15 mg/kg i.m.) before being removed from its home cage. It is placed on a heated table (36° C.) and injected with a bolus dose (5-12 mg/kg i.v.) of propofol. The animal is intubated with a cuffed endotracheal tube (4-6 mm I.D.) and anaesthesia is maintained via a continuous intravenous infusion of propofol (25-30 mg/kg/h). Vital signs (heart rate, blood pressure, respiratory rate, body temperature) are monitored throughout the experiment.

Measurements of nasal congestion: A measurement of the animal respiratory resistance is taken via a pneumotachograph connected to the endotracheal tube to ensure that it is normal. An Ecovision accoustic rhinometer is used to evaluate nasal congestion. This technique gives a non-invasive 2D echogram of the inside of the nose. The nasal volume and the minimal cross-sectional area along the length of the nasal cavity are computed within 10 seconds by a laptop computer equipped with a custom software (Hood Laboratories, Mass, U.S.A.). Nasal challenge is delivered directly to the animal's nasal cavity (50 μL volume). The changes in nasal congestion are recorded prior to and for 60-120 minutes post-challenge. If nasal congestion occurs, it will translate into a reduction in the nasal volume.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either PGD2 or Ascaris suum antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of mediator or Ascaris antigen response by the test compound. For statistical analysis, paired t-test is used. (References: McFarlane, C. S. et al., Prostaglandins, 28, 173-182 (1984) and McFarlane, C. S. et al., Agents Actions, 22, 63-68 (1987).)

Prevention of Induced Bronchoconstriction in Allergic Sheep

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.); and b) they have previously responded to inhalation challenge with *Ascaris suum* with both an acute bronchoconstriction and a late bronchial obstruction (W. M. Abraham et al., Am. Rev. Resp. Dis., 128, 839-44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10-15 breaths is used for the determination of $R_L$. Thoracic gas volume ($V_{tg}$) is measured in a body plethysmograph, to obtain specific pulmonary resistance ($SR_L = R_L \cdot V_{tg}$).

The following examples are provided to illustrate the invention and are not to be construed as limiting the scope of the invention in any manner. In the examples, unless otherwise stated, all the end products of the formula I were analyzed by NMR, TLC and elementary analysis or mass spectroscopy;
intermediates were analyzed by NMR and TLC;
most compounds were purified by flash chromatography on silica gel, recrystallization and/or swish (suspension in a solvent followed by filtration of the solid);
the course of reactions was followed by thin layer chromatography (TLC) and reaction times are given for illustration only;
the enantiomeric excess was measured on normal phase HPLC with a chiral column: ChiralPak AD; 250×4.6 mm.

The following intermediates were prepared according to literature procedures or purchased from the following vendor:

Ethyl 2-(2-oxocyclopentyl)acetate: Acros/Fisher Scientific.
4-fluoro-2-iodoaniline: Beugelmans, R.; Chbani, M. *Bull. Soc. Chim. Fr.* 1995, 132, 306-313.

EXAMPLE 1

(3R)-[4-(4-CHLOROBENZYL)-7-FLUORO-5-(METHANESULFONYL)-1,2,3,4-TETRAHYDRO-CYCLOPENTA[b]INDOL-3-YL]ACETIC ACID

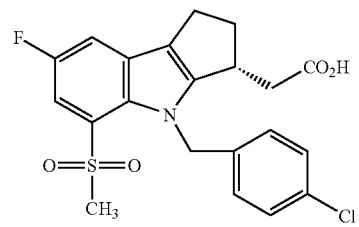

Step 1: (+/-)-(7-Fluoro-1,2,3,4-tetrahydrocyclopenta[b]indol-3-yl)acetic acid ethyl ester

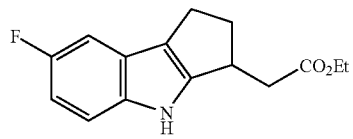

A solution of 10.00 g of 4-fluoro-2-iodoaniline, 6.57 g of ehtyl 2-(2-oxocyclopentyl)acetate and 121 mg of p-toluenesulfonic acid in 100 ml of benzene was refluxed with a Dean-Stark trap under a $N_2$ atmosphere for 24 h. After this time, the benzene was removed under distillation. Then, 60 ml of DMF was added and the solution was degassed before 19 ml of Hunig's base followed by 405 mg of Pd(OAc)$_2$ were added successively. The solution was heated to 115° C. for 3 h, then cooled to room temperature. To quench the reaction, 300 ml of 1 N HCl and 200 ml of ethyl acetate were added and the mixture was filtered through Celite. The phases were separated and the acidic phase was extracted twice with 200 ml of ethyl acetate. The organic layers were combined, washed with brine, dried over anhydrous Na$_2$SO$_4$, filtered through Celite and concentrated. The crude material was further purified by flash chromatography eluting with 100% toluene to provide 5.36 g of the title compound as a yellow solid.

$^1$H NMR (acetone-d$_6$) δ 9.76 (br s, 1H), 7.34 (dd, 1H), 7.03 (d, 1H), 6.78 (td, 1H), 4.14 (q, 2H), 3.57 (m, 1H), 2.85-2.55 (m, 5H), 2.15 (m, 1H), 1.22 (t, 3H).

Step 2: (+-)-(7-Fluoro-1,2,3,4-tetrahydrocyclopenta[b]indol-3-yl)acetic acid

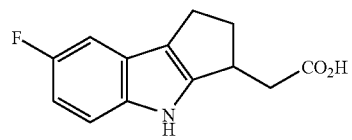

To a solution of 1.24 g of the ester from Step 1 in 14 mL of tetrahydrofuran (THF) at room temperature, 7 mL of MeOH followed by 7 mL of 2N NaOH were added. After 2.5 h, the reaction mixture was poured into a separatory funnel containing ethyl acetaqte (EtOAc)/1N HCl. The phases were separated and the acidic phase was extracted twice with EtOAc. The organic layers were combined, washed with brine, dried over anhydrous $Na_2SO_4$ and evaporated to dryness to yield 1.08 g of a crude and unstable waxy brown oil that was used as such in the next step (>90% purity).

$^1$H NMR (acetone-$d_6$) δ 10.90 (br s, 1H), 9.77 (br s, 1H), 7.34 (dd, 1H), 7.04 (dd, 1H), 6.79 (td, 1H), 3.56 (m, 1H), 2.90-2.50 (m, 5H), 2.16 (m, 1H). MS (-APCI) m/z 232.2 (M-H)$^-$.

Step 3: (+/-)-(5-bromo-7-fluoro-1,2,3,4-tetrahydrocyclopenta[b]indol-3-yl)acetic acid

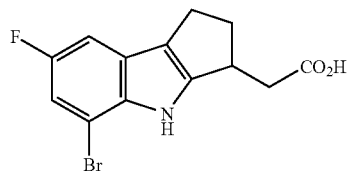

To a solution of 2.20 g of the acid from Step 2 (>90% purity) in 30 mL of pyridine, 6.85 g of pyridinium tribromide (90% purity) was added at -40° C. The suspension was stirred for 10 min at 0° C. and warmed to room temperature for 30 min. Then, the solvent was removed without heating under high vacuum. The crude material was dissolved in 40 mL of AcOH and 2.88 g of Zn dust was added portion wise to the cold solution at 0° C. The suspension was stirred for 15 min at 15° C. and warmed to room temperature for an additional 15 min. At this time, the reaction mixture was quenched by the addition of 1N HCl and this mixture was poured into a separatory funnel containing brine/EtOAc. The layers were separated and the organic layer was washed with water, brine, dried over anhydrous $Na_2SO_4$ and concentrated. This material was used without further purification in the next step.

$^1$H NMR (acetone-$d_6$) δ 10.77 (br s, 1H), 9.84 (br s, 1H), 7.09 (m, 2H), 3.60 (m, 1H), 2.95-2.65 (m, 4H), 2.56 (dd, 1H), 2.19 (m, 1H).

Step 4: (+/-)-[5-bromo-4-(4-chlorobenzyl)-7-fluoro-1,2,3,4-tetrahydrocyclopenta [b]-indol-3-yl]acetic acid

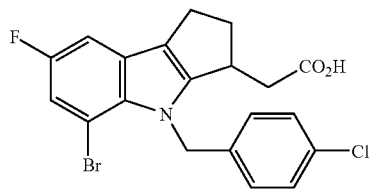

To a solution of 2.13 g of the acid from Step 3 in 10 mL of THF, a solution of diazomethane in ether was added in excess until complete consumption of the acid as monitored on TLC. Then, the solvents were removed under vacuum. To a solution of the crude methyl ester thus formed in 20 mL of DMF, 539 mg of a NaH suspension (60% in oil) was added at -78° C. The suspension was stirred for 10 min at 0° C., cooled again to -78° C. and treated with 1.70 g of 4-chlorobenzyl bromide. After 5 min, the temperature was warmed to 0° C. and the mixture was stirred for 20 min. At this time, the reaction was quenched by the addition of 2 mL of AcOH and this mixture was poured into a separatory funnel containing 1N HCl/EtOAc. The layers were separated and the organic layer was washed with brine, dried over anhydrous $Na_2SO_4$ and concentrated. The alkylated material was hydrolyzed using the procedure described in Step 2. The crude material was further purified by trituration with EtOAc/hexanes to yield 2.35 g of the title compound as a pale brown solid.

$^1$H NMR (acetone-$d_6$) δ 10.70 (br s, 1H), 7.31 (d, 2H), 7.18 (d, 1H), 7.06 (d, 1H), 6.92 (d, 2H), 5.90 (d, 1H), 5.74 (d, 1H), 3.61 (m, 1H), 3.00-2.70 (m, 3H), 2.65 (dd, 1H), 2.39 (dd, 1H), 2.26 (m, 1H). MS (-APCI) m/z 436.3, 434.5 (M-H)$^-$.

Step 5: (+/-)-[5-bromo-4-(4-chlorobenzyl)-7-fluoro-1,2,3,4-tetrahydrocyclopenta [b]-indol-3-yl}acetic acid

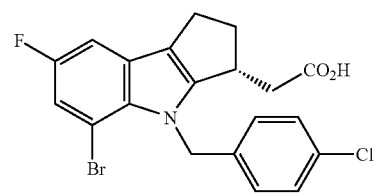

To a solution of 2.35 g of the acid of Step 4 in 130 mL of EtOH at 80° C., was added 780 μL of (S)-(-)-1-(1-naphthyl) ethylamine. The solution was cooled to room temperature and stirred overnight. The salt recovered (1.7 g) was recrystallized again with 200 mL of EtOH. After filtration, the white solid salt obtained was neutralized with 1N HCl and the product was extracted with EtOAc. The organic layer was washed with brine, dried over anhydrous $Na_2SO_4$ and concentrated. The material was filtered over a pad of $SiO_2$ by eluting with EtOAc to yield 500 mg of the title enantiomer as a white solid. Retention times of the two enantiomers were respectively 7.5 min and 9.4 min [ChiralPak AD column, hexane/2-propanol/acetic acid (95:5:0.1)]. The more polar enantiomer was in 98% ee. ee=98%; Retention time=9.4 min [ChiralPak AD column: 250×4.6 mm, hexanes/2-propanol/acetic acid (75:25:0.1)]; $[α]_D^{21}$=+39.2° (c 1.0, MeOH).

Step 6: (3R)-[4-(4-chlorobenzyl)-7-fluoro-5-(methanesulfonyl)-1,2,3,4-tetrahydro-cyclopenta[b]indol-3-yl}acetic acid and sodium salt The acid from Step 5 (15.4 g) was first esterified with diazomethane. The sulfonylation was accomplished by mixing the ester thus formed with 16.3 g of methanesulfinic acid sodium salt and 30.2 g of CuI (I) in N-methylpyrrolidinone. The suspension was degassed under a flow of $N_2$, heated to 150° C. and stirred for 3 h, then cooled to room temperature. To quench the reaction, 500 ml of ethyl acetate and 500 ml of hexanes were added and the mixture was filtered through a pad of $SiO_2$ by eluting with EtOAc. The organic phases were concentrated. The crude oil was dissolved with EtOAc, washed three times with water one time with brine, dried over anhydrous $Na_2SO_4$, filtered and concentrated. The crude material was further purified by flash chromatography eluting with a gradient from 100% toluene to 50% toluene in EtOAc to provide 14 g of the sulfonated ester, which was hydrolyzed using the procedure described in Step 2. The title compound (9.8 g) was obtained as a white solid after two successive recrystallizations: isopropyl acetate/heptane followed by $CH_2Cl_2$/hexanes.

¹H NMR (500 MHz acetone-d₆) δ 10.73 (br s, 1H), 7.57 (d, 2H, J=8.8 Hz), 7.31 (m, 1H), 7.29 (m, 1H), 6.84 (d, 2H, J=8.8 Hz), 6.29 (d, 1H, $J_{AB}$=17.8 Hz), 5.79 (d, 1H, $J_{AB}$=17.8 Hz), 3.43 (m, 1H), 2.98 (s, 3H), 2.94 (m, 1H), 2.85-2.65 (m, 3H), 2.42 (dd, 1H), $J_1$=16.1 Hz, $J_2$=10.3 Hz), 2.27 (m, 1H). ¹³C NMR (125 MHz acetone-d₆) δ 173.0, 156.5 (d, $J_{CF}$=237 Hz), 153.9, 139.2, 133.7, 133.3, 130.0 (d, $J_{CF}$=8.9 Hz), 129.6, 128.2, 127.5 (d, $J_{CF}$=7.6 Hz), 122.2 (d, $J_{CF}$=4.2 Hz), 112.3 (d, $J_{CF}$=29.4 Hz), 111.0 (d, $J_{CF}$=22.6 Hz), 50.8, 44.7, 38.6, 36.6, 36.5, 23.3. MS (−APCI) m/z 431.1, 434.1 (M−H)⁻.

ee=97%; Retention time=15.3 min [ChiralCel OD column: 250×4.6 mm, hexanes/2-propanol/ethanol/acetic acid (90:5:5:0.2)]; $[\alpha]_D^{21}$=−29.3° (c 1.0, MeOH). Mp 175.0° C.

The sodium salt was prepared by the treatment of 6.45 g (14.80 mmol) of the above acid compound in EtOH (100 mL) with 14.80 mL of an aqueous 1N NaOH solution. The organic solvent was removed under vacuum and the crude solid was dissolved in 1.2 L of isopropyl alcohol under reflux. The final volume was reduced to 500 mL by distillation of the solvent. The sodium salt crystallized by cooling to rt. The crystalline sodium salt was suspended in H₂O, frozen with a dry ice bath and lyophilized under high vacuum to give 6.00 g of the title compound as the sodium salt.

¹H NMR (500 MHz DMSO-d₆) δ 7.63 (dd, 1H, $J_1$=8.5 Hz, $J_2$=2.6 Hz), 7.47 (dd, 1H, $J_1$=9.7 Hz, $J_2$=2.6 Hz), 7.33 (d, 2H, J=8.4 Hz), 6.70 (d, 2H, J=8.4 Hz), 6.06 (d, 1H, $J_{AB}$=17.9 Hz), 5.76 (d, 1H, $J_{AB}$=17.9 Hz), 3.29 (m, 1H), 3.08 (s, 3H), 2.80 (m, 1H), 2.69 (m, 1H), 2.55 (m, 1H), 2.18 (m, 2H), 1.93 (dd, 1H, $J_1$=14.4 Hz, $J_2$=9.7 Hz).

EXAMPLE 1A

Alternative procedure for (+/−)-[5-bromo-4-(4-chlorobenzyl)-7-fluoro-1,2,3,4-tetrahydrocyclopenta[b]indol-3-yl]acetic acid (Example 1, Step 4)

Step 1: (+/−)-7-fluoro-1,2,3,4-tetrahydrocyclopenta[b]indol-3-yl)acetic acid dicyclohexylamine (DCHA) salt A 0.526 M solution of 2-bromo-4-fluoroaniline in xylene along with ethyl (2-oxocyclopentyl) acetate (1.5 eq) and sulfuric acid (0.02 eq) was heated to reflux for 20 hours. Water was azeotropically removed with a Dean-Stark apparatus. The reaction was followed by NMR and after 20 hours, a 80-85% conversion to the desired imine intermediate was generally observed. The reaction mixture was washed with 1M sodium bicarbonate (0.2 volumes) for 15 minutes and the organic fraction was evaporated. The remaining syrup was distilled under vacuum (0.5 mm Hg). Residual xylenes distilled at 30° C., then excess ketone and unreacted aniline were recovered in 50-110° C. range; the imine was recovered in the 110-180° C. fraction as a light brown clear liquid with 83% purity.

The imine intermediate was then added to a degased mixture of potassium acetate (3 eq), tetra-n-butylammonium chloride monohydrate (1 eq), palladium acetate (0.03 eq) and N,N-dimethylacetamide (final concentration of imine=0.365 M). The reaction mixture was heated to 115° C. for 5 hours and allowed to cool to room temperature. 3N KOH (3 eq) was then added and the mixture was stirred at room temperature for 1 hour. The reaction mixture was diluted with water (1.0 volume), washed with toluene (3×0.75 volume). The aqueous phase was acidified to pH 1 with 3N HCl and extracted with tertbutyl methyl ether (2×0.75 volume). The combined organic fractions were washed with water (0.75 volume). To the clear light brown solution was added dicyclohexylamine (1 eq) and the solution was stirred at room temperature for 16 hours. The salt was filtered, washed with ethyl acetate, tertbutyl methyl ether and allowed to dry to give the title compound as a tan solid. Assay: 94 A %.

1H NMR (500 mHz, CDCl3): δ 9.24 (s, 1H), 7.16-7.08 (m, 2H), 6.82 (t, 1H), 6.2 (br, 2H), 3.6-3.5 (m, 1H), 3.04-2.97 (m, 2H), 2.88-2.70 (m, 3H), 2.66 (dd, 1H), 2.45-2.37 (m, 1H), 2.13-2.05 (m, 2.05), 1.83 (d, 4H), 1.67 (d, 2H), 1.55-1.43 (m, 4H), 1.33-1.11 (m, 6H).

Step 2: (+/−)-(5-bromo-7-fluoro-1,2,3,4-tetrahydrocyclopenta[b]indol-3-yl)acetic acid A slurry of the DCHA salt from Step 1 above in dichloromethane (0.241 M solution) was cooled to −20 to −15° C. Pyridine (2 eq.) was added in one shot and to the slurry was added dropwise bromine (2.5 eq.) over 30 to 45 minutes maintaining the temperature between −20° C. and −15° C. (At about ⅓ addition of bromine, the reaction mixture was thick and an efficient stirring was needed. Eventually, at about ½ addition of bromine, the mixture became "loose" again.) After completion of the addition, the reaction mixture was aged for one additional hour at −15° C. Acetic acid (3.04 eq.) was then added over 5 minutes and zinc dust (3.04 eq.) was added portion wise. (A portion of zinc was added at −15° C. and the mixture was aged for about 5 minutes to ensure that the exotherm was going (about −15° C. to −10° C.)). This operation was repeated with about 5 shots of zinc over about 30 min. When no more exotherm was observed, the remaining zinc was added faster. The whole operation takes around 30 to 45 minutes.

After completion of the addition, the batch was warmed to room temperature, aged 1 hour and concentrated. The reaction mixture was switched to methyl t-butyl ether (MTBE, 0.8 volume) and a 10% aqueous acetic acid solution (0.8 volume) was added. The mixture (crystallization of salts, e.g pyridium) was aged at room temperature for 1 hour and filtered through solka-floc. The pad of solka-floc was rinsed with MTBE (ca. 0.2 volume) and the filtrate (biphasic, MTBE/aqueous) was transferred into an extractor. The organic phase was washed with water (0.8 volume). The MTBE extract was concentrated and switched to isopropyl alcohol (IPA, 0.25 volume) to crystallize the compound. water (0.25 volumes) was added and the batch was aged for 1 hour. Additional water (0.33 volumes) was added over 1 hour. After completion of the water addition, the batch was aged for one additionnal hour, filtered, and rinse with 30/70 IPA/Water (0.15 volumes). Crystallized bromoacid was dried in the oven at +45° C.

Step 3: (+/−)-[5-bromo-4-(4-chlorobenzyl)-7-fluoro-1,2,3,4-tetrahydrocyclopenta[b]-indol-3-yl]acetic acid The bromoacid of Step 2 was dissolved in dimethylacetamide (0.416 M solution) and cesium carbonate (2.5 eq.) was added in one portion. To the slurry was added in one portion 4-chlorobenzyl chloride (2.5 eq.) and the batch was heated to 50° C. for 20 h. The batch was cooled to r.t. and sodium hydroxide 5N (4.00 eq.) was added over 5 minutes (temperature rises to +40° C.). The reaction was aged at 50° C. for ca. 3 hours, cooled to room temperature and transferred into an L extractor. The solution was diluted with isopropylacetate (IPAc, 2 volumes) and cooled to +15° C. The solution was acidified with 5N HCl to pH~2. Layers are separated and the organic layer was washed with water (2×2 volumes). IPAc solution was concentrated and switched to IPA (0.8 volumes) to crystallize the product. Water (8 L) was added over 2 hours and the batch was filtered to give the title compound in 88% isolated yield. The batch can be dried in the oven at +40° C. for 24 hours.

EXAMPLE 2

(+/−)-{4-[1-(4-CHLOROPHENYL)ETHYL]-7-FLUORO-5-METHANESULFONYL-1,2,3,4-TETRAHYDRO-CYCLOPENTA[B]INDOL-3-YL}ACETIC AICD

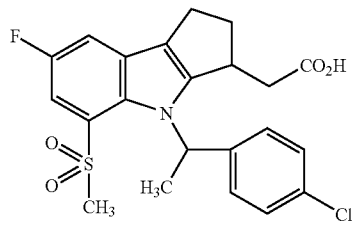

To a solution of 1.5 g of the methyl ester of the acid of Example 1, Step 3 (which was prepared by esterification of the corresponding acid with diazomethane in tetrahydrofuran), 2.03 g of 1-(1-bromoethyl)-4-chlorobenzene in 50 mL of acetonitrile and 6.01 g of cesium carbonate was added. The resulting mixture was heated to reflux with rigorous stirring for 3 hr. Then the reaction mixture was cooled to room temperature, diluted with 50 mL of ethyl acetate, filtered, and the solvent evaporated. The residue was purified by flash chromatography (silica gel, 4% EtOAc/hexane) to afford 1.41 g of desired N-benzylation product as an approximate 1:1 mixture of diastereomers according to $^1$H NMR analysis.

To the above ester (1.2 g) dissolved in 80 mL of NMP, 2.63 g of methanesulfinic acid sodium salt and 3.7 g of Cu(I)Br was added successively. The resulting suspension was degassed under a flow of $N_2$, heated to 140° C. and stirred rigorously for 8 h. Then the reaction mixture was cooled to room temperature and diluted with 500 ml of ethyl acetate and 500 ml of hexane. The resulting mixture was filtered through a pad of silica gel, further eluted with EtOAc. The filtrate was concentrated to about 300 mL of volume and washed with water and brine. The organic phase was separated and dried over anhydrous $Na_2SO_4$, filtered, and concentrated. The crude material was further purified by flash chromatography over silica gel eluting with 30% EtOAc/hexane to provide 1.0 g of the sulfonated material. It was hydrolyzed to its corresponding acid using 10 mL of 2 N NaOH in a solvent mixture composed of 10 mL of THF and 10 mL of MeOH at rt for 3 h. The reaction mixture was neutralized with 1 M HCl aqueous solution and extracted-with EtOAc. The separated organic phase was dried over anhydrous sodium sulfate, filtered, and evaporated to afford the crude acid. The two diastereomers were separated by using preparative BPLC (Zobax, 30% EtOAC/hexane with 0.2% AcOH) to afford 300 mg of diastereomer A (shorter retention time) and 210 mg of diastereomer B (longer retention time).

Diastereomer B: $^1$H NMR (acetone-$d_6$) δ 10.70 (br s, 1H), 7.66 (dd, 1H), 7.56 (dd, 1H), 7.32 (d, 2H), 6.95 (d, 2H), 6.91 (q, 1H), 3.39 (s, 3H), 3.05-3.00 (m, 1H), 2.90-2.75 (m, 2 H), 2.70 (dd, 1H), 2.44 (dd, 1H), 2.43-2.34 (m, 1H), 2.21 (dd, 1H) 2.11 (d, 3H). MS (−APCI) m/z 448.0(M−H)$^-$.

EXAMPLE 2A

Alternative synthesis of (+/−)-4-[1-(4-chlorophenyl)ethyl]-7-fluoro-5-methane-sulfonyl-1, 2,3,4-tetrahydro-cyclopenta[b]indol-3-yl}acetic acid To a solution of 6.52 g of the methyl ester of the acid of Example 1, Step 3 (which was prepared by esterification of the corresponding acid with diazomethane in tetrahydrofuran) in 160 mL of NMP, 10.2 g of methanesulfinic acid sodium salt and 19 g of CuI was added successively. The resulting suspension was degassed under a flow of $N_2$, heated to 150° C. and stirred rigorously for 4 h. Then the reaction mixture was cooled to room temperature and diluted with 500 ml of ethyl acetate and 500 ml of hexane. The resulting mixture was filtered through a pad of silica gel, further eluted with EtOAc. The filtrate was concentrated to about 300 mL of volume and washed with water and brine. The organic phase was separated and dried over anhydrous $Na_2SO_4$, filtered, and concentrated. The crude material was further purified by flash chromatography over silica gel eluting with 30% EtOAc/hexane to provide 4.7 g of the sulfonated material, which was dissolved in 200 mL of dichloromethane. To the resulting solution, 3.39 g of 4-chlorophenyl methyl carbinol and 5.68 g of triphenylphosphine was added, followed by the portion-wise addition of 4.99 g of di-tert-butyl azodicarboxylate. The reaction mixture was stirred at rt for 3 h and then concentrated. The residue was loaded on a silica gel column and eluted with 5% EtOAc/hexane to afford 5.1 g of methyl ester of the title compound as an approximately 1:1 mixture of diastereomers according to $^1$H NMR analysis. Following the hydrolysis and purification step described in Example 2, the title acid was afforded.

EXAMPLE 3

(+/−)-[9-(4-CHLOROBENZYL)-6-FLUORO-8-METHANESULFONYL-2,3,4,9-TETRAHYDRO-1H-CARBAZOL-1-YL]ACETIC ACID

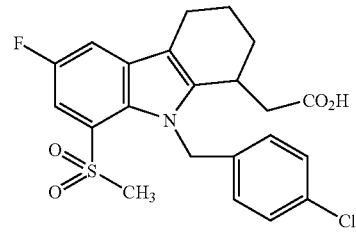

Step 1: (+/−)-ethyl (8-bromo-6-fluoro-2,3,4,9-tetrahydro-1H-carbazol-1-yl)acetate

To a suspension of 7.24 g of (2-bromo-4-fluorophenyl) hydrazine hydrochloric acid salt in 100 mL of acetic acid, 5.5 g of ethyl 2-(2-oxocyclohexyl)-acetate was added. The resulting mixture was heated to reflux for 1 h. Then 10 mL of ethanol was added and the reaction mixture was heated at reflux overnight. The solvent was evaporated and the residue was diluted with EtOAc and washed with saturated aqueous NaHCO$_3$ solution, water, and brine successively. The organic layer was separated and dried over anhydrous sodium sulfate, filtered, and evaporated. The residue was purified by flash chromatography over silica gel (5% EtOAc/hexane) to afford 3.12 g of desired compound.

$^1$H NMR (acetone-d$_6$) δ 9.97 (br s, 1H), 7.34 (dd, 1H), 7.13 (dd, 1H), 7.09 (dd, 1H), 4.16 (q, 2H), 3.43-3.35 (m, 5H), 3.05-2.88 (m, 1H), 2.76-2.53 (m, 3H), 2.10-2.00 (m, 1H), 1.96-1.87 (m, 1H), 1.82-1.72 (m, H), 1.72-1.64 (m, 1H), 1.23 (t, 3H).

Step 2: (+/−)-Ethyl[8-Bromo-9-(4-chlorobenzyl)-6-fluoro-2,3,4,9-tetrahydro-1H-carbazol-1-yl]acetate

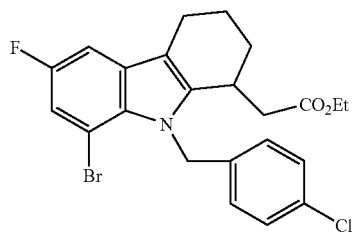

To a solution of 3.12 g of the ester prepared in step 1 and 3.62 g of 1-bromomethyl-4-chlorobenzene in 30 mL of acetonitrile, 5.74 g of cesium carbonate was added. The resulting mixture was stirred rigorously at reflux for 3 hr. Then it was cooled to room temperature, diluted with minimum amount of EtOAc, filtered, and evaporated. The residue was purified by flash chromatography over silica gel (50% toluene/hexane) to afford 4.1 g of the title compound.

$^1$H NMR (acetone-d$_6$) δ 7.32 (d, 2H), 7.24 (dd, 1H), 7.13 (dd, 1H), 6.86 (d, 2H), 6.00 and 5.65 (AB q, 2H), 4.15-4.05 (m, 2H), 3.44-3.35 (m, 1H), 2.88-2.76 (m, 1H, 2.65-2.52 (m, 3H), 2.00-1.80 (m, 4H), 1.22 (t, 3H).

Step 3: (+/−)-[9-(4-Chlorobenzyl)-6-fluoro-8-methanesulfonyl-2,3,4,9-tetrahydro-1H-carbazol-1-yl]acetic acid To a solution of 478 mg of the ester prepared in step 2 in 8 mL of NMP, 510 mg of methanesulfinic acid sodium salt and 950 mg of CuI (I) was added successively. The resulting mixture was degassed under a flow of N$_2$, then heated at 140° C. for 8 h under rigorous stirring. The reaction mixture was cooled to room temperature, diluted with minimum amount of a 1:1 mixture of EtOAc/hexane. The resulting mixture was filtered through a pad of silica gel, further eluted with EtOAc. The filtrate was concentrated to about 50 mL, and washed with water and brine. The organic phase was collected, dried over anhydrous sodium sulfate, filtered, and evaporated. The residue was purified by flash chromatography over silica gel (30% EtOAc/hexane) to afford 320 mg of desired sulfonated material, which was dissolved in 5 mL of THF plus 5 mL of methanol. To the resulting solution, 5 mL of 2 N of NaOH was added and the resulting mixture was stirred at rt for 6 h. The reaction mixture was neutralized with 1 M HCl aqueous solution and extracted with EtOAc. The separated organic phase was dried over anhydrous sodium sulfate, filtered, and evaporated. The residue was refluxed with hexane under rigorous stirring for 0.5 h. The resulting mixture was cooled to rt under rigorous stirring, and filtered to afford 278 mg of desired acid.

$^1$H NMR (500 MHz acetone-d$_6$) δ 10.73 (br s, 1H), 7.57 (d, 1H), 7.56 (d, 1H), 7.29 (d, 1H), 6.67 (d, 2H,), 6.47 and 5.61 (AB q, 2H), 3.27-3.21(m, 1H), 2.98 (s, 3H), 2.85 (dd, 1H), 2.76-2.55 (m, 3H), 2.00-1.84 (m, 3H), 1.82-1.73 (m, 1H). MS (−APCI) m/z 448.0 (M−H)$^-$.

EXAMPLE 4

[4-(4-CHLOROBENZYL)-7-FLUORO-5-METH-ANESULFONYL-1-OXO-1,2,3,4-TETRAHYDRO-CYCLOPENTA[B]INDOL-3-YL]ACETIC ACID

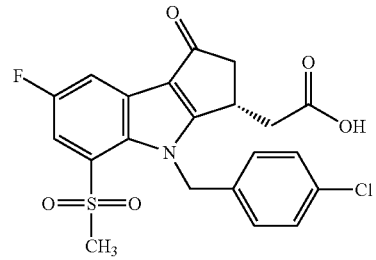

Step 1: [5-Bromo-4-(4-chlorobenzyl)-7-fluoro-1-oxo-1,2,3,4-tetrahydro-cyclopenta[b]indol-3-yl]acetic acid methyl ester

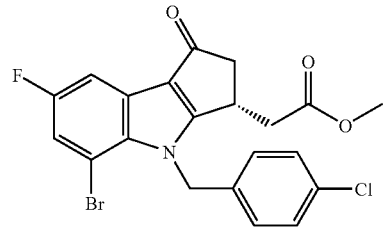

The methyl ester of the compound of Example 1 step 5 (1.00 g, preapared by treating the corresponding acid with excess diazomethane) in 10 mL of a 9:1 THF/H$_2$O solution was treated with 2.52 g of DDQ. The reaction mixture was allowed to stir at room temperature overnight. The reaction mixture at this time was poured into a separatory funnel containing EtOAc and brine. The combined organic layers were washed with water, brine, dried over anhydrous MgSO$_4$ and concentrated. The resulting material was further purified by flash chromatography eluting with 30% EtOAc/hexane. The chromatography procedure was repeated an additional two times. 350 mg of the above ketone was obtained as a grey solid.

Step 2: [4-(4-chlorobenzyl)-7-fluoro-5-methanesulfonyl-1-oxo-1,2,3,4-tetrahydro-cyclopenta[b]indol-3-yl]acetic acid The bromide from Step 1 (200 mg) in 4 mL of NMP was treated with 320 mg of CuI and 175 mg of CH$_3$SO$_2$Na. Nitrogen was bubbled through the reaction mixture for approximately one minute and then the mixture was heated for six hours at 130° C. At this time the reaction mixture was cooled to room temperature, diluted with EtOAc and filtered through a pad of silica gel, the residue was rinsed with additional EtOAc. The organic layers were washed with water, brine, dried over anhydrous MgSO$_4$ and concentrated. The resulting oil was purified by flash chromatography eluting with 50% EtOAc/hexane and obtained 54 mg of the corresponding methyl sulphone as an off-white solid.

The above methyl ester in 5 mL of THF/H$_2$O (1:1) and 5 mL of MeOH was treated with 1 mL of a 1 N HCl solution. This mixture was stirred at room temperature for two hours. At this time the reaction mixture was acidified with a 1N HCl solution and poured into a separatory funnel containing water and EtOAc. The layers were separated and the aqueous layer was extracted EtOAc. The combined organic layers were washed with water, brine, dried over anhydrous Na$_2$SO$_4$ and concentrated. The resulting material was further purified by flash chromatography eluting with 100% EtOAc containing 1% AcOH and 26 mg of the title acid was obtained as an off white solid.

$^1$H NMR (500 MHz, acetone-d$_6$) δ 11.0 (br, 1H), 7.85 (m, 1H), 7.80 (m, 1H), 7.38 (d, J=8 Hz, 2H), 7.04 (d, J=8 Hz, 2H), 6.42 (d, J$_{AB}$=18 Hz, 1H), 6.08 (d, J$_{AB}$=18 Hz, 1H), 3.78 (m, 1H), 3.28 (m, 1H), 3.10 (m, 1H), 3.05 (s, 3H), 2.65 (m, 2H). MS (−APCI) m/z 448.2 (M−H)−.

What is claimed is:

1. A compound of the formula:

or a pharmaceutically acceptable salt thereof.

2. A pharmaceutical composition comprised of a compound in accordance with claim 1 further comprising a pharmaceutically acceptable carrier.

3. A pharmaceutical composition in accordance with claim 2 further comprising nicotinic acid.

4. A compound of the formula:

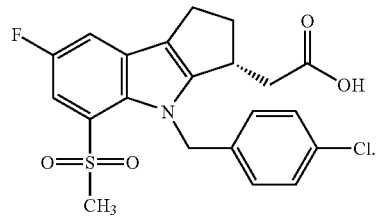

5. A pharmaceutical composition comprised of a compound in accordance with claim 4 further comprising a pharmaceutically acceptable carrier.

6. A pharmaceutical composition on accordance with claim 5 further comprising nicotinic acid.

* * * * *